United States Patent
Ono et al.

(10) Patent No.: US 6,459,004 B1
(45) Date of Patent: Oct. 1, 2002

(54) CLEAVAGE METHOD OF BISPHENOLS

(75) Inventors: Yuzo Ono, Aichi; Kouichirou Terada, Fukuoka; Kiyoshi Mizuma; Mikio Shibasaki, both of Aichi, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/763,547

(22) PCT Filed: Jul. 4, 2000

(86) PCT No.: PCT/JP00/04429

§ 371 (c)(1),
(2), (4) Date: Feb. 23, 2001

(87) PCT Pub. No.: WO01/02331

PCT Pub. Date: Jan. 11, 2001

(30) Foreign Application Priority Data

Jul. 6, 1999 (JP) .......................................... 11-191241

(51) Int. Cl.[7] .............................................. C07C 37/52
(52) U.S. Cl. ........................................ 568/728; 568/806
(58) Field of Search ................................. 568/806, 728

(56) References Cited

U.S. PATENT DOCUMENTS

| | | | | | |
|---|---|---|---|---|---|
| 3,466,337 A | * | 9/1969 | Smith | .......................... | 568/806 |
| 4,054,611 A | | 10/1977 | Mimaki et al. | | |
| 4,245,128 A | * | 1/1981 | Kato | ........................... | 568/743 |
| 4,277,628 A | * | 7/1981 | Carahan | ...................... | 568/749 |
| 4,351,966 A | * | 9/1982 | Flock | .......................... | 568/753 |
| 4,657,890 A | * | 4/1987 | Graces | ........................ | 568/806 |
| 4,717,777 A | * | 1/1988 | Graces | ........................ | 568/806 |
| 4,754,081 A | * | 6/1988 | Mott | ............................ | 568/806 |
| 4,873,376 A | | 10/1989 | Dujardin et al. | | |
| 5,504,251 A | * | 4/1996 | Dyckman | .................... | 568/724 |
| 5,723,689 A | | 3/1998 | Pressman et al. | | |

FOREIGN PATENT DOCUMENTS

| | | |
|---|---|---|
| JP | 37-13064 | 9/1962 |
| JP | 50-13341 | 2/1975 |
| JP | 54-84536 | 7/1979 |
| JP | 55-49331 | 4/1980 |
| JP | 62-148441 | 7/1987 |
| JP | 64-29332 | 1/1989 |
| JP | 4-9347 | 1/1992 |
| JP | 2000-191576 | 1/1999 |

OTHER PUBLICATIONS

S.H. Dai et al, "Selective Indirect Oxidation of Phenol to Hydroquinone and Catechol", J. Org. Chem., vol. 50, No. 10, pp. 1722–1725, 1985.

* cited by examiner

Primary Examiner—Michael L. Shippen
(74) Attorney, Agent, or Firm—Burns, Doane, Swecker & Mathis, L.L.P.

(57) ABSTRACT

A cleavage method of bisphenols capable of yielding a product containing high-purity isopropenylphenol and phenol is disclosed, including (1) a cleavage step of supplying the mixture containing bisphenols together with chroman derivatives and flavan derivatives formed as by-products in the production process of bisphenols to a cleaving vessel and carrying out a cleavage reaction in the presence of a basic or acidic catalyst at a temperature of from 150 to 260° C. under a reduced pressure condition of not higher than 300 mmHg, (2) a distillation step of supplying the cleavage step product formed in the cleavage step in a vapor state to a distillation column and distilling at a temperature of from 130 to 200° C. under a reduced pressure condition of not higher than 300 mmHg, and (3) a reflux step of condensing the distillate from the distillation step, refluxing a part thereof to the distillation step at a reflux ratio of from 0.01 to 3, and discharging out the residue from the system.

26 Claims, No Drawings

CLEAVAGE METHOD OF BISPHENOLS

BACKGROUND OF THE INVENTION

1. Field of the Invention

The present invention relates to a cleavage method of bisphenols. More specifically, the invention relates to a cleavage method of bisphenols capable of producing cleavage products made of isopropenylphenol and phenol as main constituents at high purity by cleaving a mixture containing bisphenols and impurities such as chroman derivatives and flavan derivatives formed as by-products in the production process of bisphenols.

The cleavage product obtained by the method of the invention contains isopropenylphenol and phenol together with small amounts of impurities. Usually, the product is circulated to a production step of bisphenols as it is and then reproduced to bisphenols. The invention is preferably applied to the cleavage of a mixture containing bisphenol A and impurities formed as by-products in the production process of bisphenol A, such as chroman derivatives and flavan derivatives.

2. Description of the Related Art

It is known that, when bisphenol A or a bisphenol A-containing compound is heated in the presence of a catalyst, a cleavage reaction proceeds to form phenol, 4-isopropenylphenol, and 4-isopropenylphenol polymers, etc.

Usually, the cleavage reaction is carried out in the presence of a basic catalyst or an acidic catalyst at a high temperature of from 150 to 260° C. under a reduced pressure condition (for example, Japanese Patent Laid-Open Nos. 27108/1980 and 148441/1987).

4-Isopropenylphenol has a very high reactivity, and particularly, in the case where it is in a liquid state, the polymerization occurs quickly to cause lowering of the cleavage yield. Accordingly, in the conventional technology, the cleavage product made of 4-isopropenylphenol and phenol as major components is distilled out in a vapor state from a reaction vessel, and operations such as distillation for purification are not carried out. For this reason, various kinds of impurities contained in cleavage raw materials and/or formed as by-products during the cleavage reaction are incorporated in the cleavage distillate to cause lowering of the purity of the cleavage product.

Usually, a cleavage reaction product is circulated to a production step of bisphenol A as it is and then reproduced to bisphenol A. For this reason, when the cleavage reaction product contains a large amount of impurities, it causes lowering of the purity of bisphenol A produced. Also, it causes lowering of the production efficiency of bisphenol A. Isopropenylphenol is a very unstable substance, and generally, it has been said that in the distillation for purification, the yield of isopropenylphenol is lowered, and the distillation column is clogged by a dimer of isopropenylphenol, etc. formed as by-products. For this reason, in the conventional technology, the distillation for purification is not carried out, and the cleavage reaction product is used for the above-described utilization as it is.

SUMMARY OF THE INVENTION

In view of the above-described circumstances, the invention has been made, and an object of the invention is to provide a cleavage method of bisphenols capable of yielding a product containing high-purity isopropenylphenol and phenol.

As the result of various investigations, the present inventors have found that by supplying a cleavage reaction product in a vapor state to a distillation column and carrying out a cleavage reaction of bisphenols while distilling at a specific reflux ratio without disposing a heating source such as a reboiler in a distillation step, the above-described object can be attained, leading to accomplishment of the invention.

Specifically, the invention is to provide a cleavage method of bisphenols for producing a product containing isopropenylphenol and phenol by cleaving a mixture containing bisphenols together with chroman derivatives and flavan derivatives formed as by-products in the production process of bisphenols, which comprises (1) a cleavage step of supplying the mixture containing bisphenols together with chroman derivatives and flavan derivatives formed as by-products in the production process of bisphenols to a cleaving vessel and carrying out a cleavage reaction in the presence of a basic or acidic catalyst at a temperature of from 150 to 260° C. under a reduced pressure condition of not higher than 300 mmHg, (2) a distillation step of supplying the cleavage step product in a vapor state in the cleavage step to a distillation column and distilling at a temperature of from 130 to 200° C. and under a reduced pressure condition of not higher than 300 mmHg, and (3) a reflux step of condensing the distillate formed in the distillation step, refluxing a part thereof to the distillation step at a reflux ratio of from 0.01 to 3, and discharging out the rests from the system.

The feature of the invention resides in that in the above-described constructions, particularly, the cleavage reaction product is supplied in a vapor state to a distillation column, and the cleavage reaction of bisphenols is carried out while distilling at a specific reflux ratio without disposing a heating source such as a reboiler to the distillation step. In addition, as preferred embodiments of the invention, there are included the above-described cleavage method of returning the bottom liquid of the distillation step to the cleavage step; the above-described cleavage method by side cutting at least 1% by weight of the reflux liquid of the distillation column and discharging out the reflux liquid from the system; the above-described cleavage method of introducing the distillate (reflux residue) of the reflux step to the bisphenol production step and recovering, etc. A method to which the invention is preferably applied is the cleavage method of the mixture containing bisphenol A together with impurities formed as by-products in the production process of bisphenols A, such as chroman derivatives and flavan derivatives.

According to the invention, because the cleavage reaction product is supplied in a vapor state to the distillation column, the occurrence of polymerization of highly reactive isopropenylphenol is prevented, whereby the formation of oligomers such as dimers and trimers can be restrained. Accordingly, it is possible to yield high-purity phenol and isopropenylphenol, and further, even when the distillate (reflux residue) of the reflux step is circulated to, for example, the production step of bisphenol A, etc., the quality of the bisphenol A as the product is not lowered, resulting in rather improving the purity and reducing the production cost.

DETAILED DESCRIPTION OF THE INVENTION

The invention is described below in detail.

The invention relates to a cleavage method of bisphenols by supplying a mixture containing bisphenols and impurities formed as by-products in the production process of bisphenols, such as chroman derivatives and flavan derivatives, to a cleaving vessel to cleave the mixture, supplying the cleavage product in a vapor state to the distillation column, and distilling the product while refluxing at a specific reflux ratio to produce a product containing isopropenylphenol and phenol.

As the cleavage reaction raw materials in the invention, a mixture containing bisphenols such as bisphenol A and bisphenol F and impurities formed as by-products in the production process of the bisphenols, such as chroman derivatives and flavan derivatives. Examples include an effluent from the distillation column of bisphenol A obtained in the production step of bisphenol A and a crystallization mother liquor of bisphenol A from which phenol has been removed. Hereinafter, these are generally called "bisphenols".

The cleavage reaction method of the invention is a method of obtaining a cleavage reaction product made of 4-isopropenylphenol and phenol as major components by cleaving bisphenols, and generally, the cleavage reaction is carried out in the presence of a basic catalyst or an acidic catalyst at a temperature of from 150 to 260° C. under a reduced pressure of not higher than 300 mmHg. Also, in order to improve the yield, bubbling of an inert gas may be continuously carried out from a lower portion of the reaction vessel. A supplying method of the cleavage reaction raw materials to the cleavage reaction vessel may be continuous or intermittent, but a continuous supply is preferred.

As the catalyst for the cleavage reaction, a basic catalyst or an acidic catalyst is used. The basic catalyst includes oxides, hydroxides and carbonates of an alkali metal or an alkaline earth metal. Examples include sodium hydroxide, potassium hydroxide, calcium hydroxide, sodium carbonate, potassium carbonate, and calcium oxide. The acidic catalyst includes aluminum chloride, zirconium chloride, and zirconium sulfate. In general, the basic catalyst is preferred. A using amount of the catalyst is preferably from about 0.001 to 1% by weight of the bisphenols as the cleavage reaction raw materials.

As described above, for example, 4-isopropenylphenol produced by the cleavage reaction has a very high reactivity, and particularly, when the product is in a liquid form, a polymerization reaction occurs quickly, oligomers, such as dimers and trimers, of 4-isopropenylphenol are formed. Taking into consideration the yields of 4-isopropenylphenol and phenol, in the case of distilling out the cleavage reaction product from the cleavage reaction vessel, the product is preferably in a vapor state, and it is desired that the liquid-phase portion is as small as possible. From such a view point, in the invention, distillation of a reboiler system disposed to an ordinary distillation column is not preferred. In the invention, the cleavage reaction product is introduced into a distillation column in a state of vapor. In this case, the state of vapor may be in a state containing liquid-phase mists if the amount thereof is small. Specifically, when the amount of the mists is not more than 30% by weight, and preferably not more than 10% by weight, the vapor state may be one containing the liquid-phase mists.

The distillation column includes a packed column-type distillation column, a thin film-type distillation column, and a partial condenser-type distillation column. The supplying stage of the cleavage product to the distillation column may be an intermediate stage of the column but is preferably a column bottom. The distillation column may be disposed in an upper portion of the cleavage reaction vessel, or may be disposed independently from the cleavage reaction vessel. But taking into consideration the occurrence of aggregation, liquefaction, etc. in supplying the cleavage product in a vapor state to the distillation column, it is preferred that the distillation column is disposed in an upper portion of the cleavage reaction vessel. The stage number of the distillation column may be a condition under which high-boiling substances such as a 4-isopropenylphenol dimer can be separated from 4-isopropenylphenol and phenol. An increase of the residence time of the liquid in the distillation column causes a reduction of the yields of 4-isopropenylphenol, etc. Therefore, it is desired that the residence time of the liquid in a rectifying portion of the distillation column is short. In general, a distillation column having from 1 to 10 stages in terms of theoretical stages is used. Thus, the distillation column may be a plate column, but a packed column system giving less hold up amount of the liquid and being excellent in the operability is preferred. Also, as the case may be, a thin-film distillation system or a partial condenser system may be used.

It is preferred to dispose a demister for preventing entrainment of the liquid mists in a lower portion of the distillation column. This is because in the distillation column of a packed column system, due to impurities contained in liquid mists, which are easily solidified, the packed material causes clogging and channeling, leading to lowering of the distillation efficiency and a reduction of the operation stability of the distillation column. Also, in the case of a thin-film distillation column or a partial condenser, it is preferred to dispose a demister in an outlet portion of the partial condensation vapor in order to prevent lowering of the purity by the liquid mists. As the demister disposed in a lower portion, a liquid collector-type demister is preferably used.

The operation temperature of the distillation column is preferably as low as possible from the viewpoint of the reactivity of 4-isopropenylphenol. However, a low-temperature operation may cause the formation of solid materials and clogging by oligomers, such a dimer and a the trimer, of 4-isopropenylphenol. On the other hand, the temperature of the distillation column is determined by a vapor-liquid equilibrium, and because the vapor composition is not largely changed, the increase of the temperature of the distillation column increases the cleaving pressure. The pressure of the cleavage vessel is required to be a proper reduced pressure from the relation with the cleaving yield. For this reason, when the temperature is too increased, the yield of 4-isopropenylphenol is lowered.

As the result of making various investigations taking into consideration these matters, it has been found that by operating the distillation column at a temperature in the column in the range of from 130 to 200° C. at which the decomposition of the 4-isopropenylphenol dimer, etc. starts without solidifying the above-described oligomers, the impurities such as chroman derivatives and flavan derivatives can be separated and removed without causing the formation of solid materials, clogging, and lowering of the yield of 4-isopropenylphenol. It is desired that the pressure of the distillation column is not higher than 300 mmHg.

The cleavage product distilled out from the distillation column is condensed, and a part thereof is refluxed to the distillation column. The reflux liquid may be a part of the total-condensed liquid in a total condenser or a part or the all of the partial-condensed liquid in a partial condenser. Usually, such a condensed liquid is refluxed to the distillation column through a receiver for the condensed liquid. In this case, in the receiver for the condensed liquid or even in the condenser, a part of 4-isopropenylphenol becomes an oligomer such as a dimer and a trimer. Such low polymerized products are liable to be solidified as compared with 4-isopropenylphenol and phenol, so that it causes the formation of solid materials and clogging of the distillation column. Accordingly, it is desired that the residence time of the liquid in the condenser and the receiver for the condensed liquid is as short as possible.

It is undesirable that the reflux amount is too large or too small. When the reflux amount is too large, it causes lowering of the yield of 4-isopropenylphenol and the formation of solid materials and clogging of the distillation column by oligomers of 4-isopropenylphenol. On the contrary, when the reflux amount is too small, it is undesirable from the standpoint of the effect of the distillation for purification. Considering these points, the reflux ratio is preferably in the range of from 0.01 to 3, and more preferably in the rage of from 0.05 to 1. In the case, the reflux ratio as referred to herein shows a ratio of (the weight of reflux liquid) to{ (the total weight of distilled out vapors)—(the weight of refluxed liquid)}.

In the cleavage product obtained by the method of this invention, the contents of chroman derivatives and flavan derivatives which are difficult to be separated in the production process of bisphenols such as bisphenol A are greatly reduced. Therefore, it is possible to improve the purity of bisphenol A as compared with the method of the related art wherein the purification of the cleavage product is not carried out. Furthermore, because the circulating amounts of impurities are reduced in the method of the invention, the production cost of bisphenol A, etc. is reduced. Particularly, in the operation at a definite purity, the effect of rationalization becomes more large.

On the other hand, the bottom liquid of the distillation column may be discharged from the system, but taking into consideration the yield of 4-isopropenylphenol, it is efficient to return the liquid to the cleavage reaction vessel. High-boiling compounds derived from 4-isopropenylphenol and phenol returned to the cleavage reaction vessel are cleaved again to form 4-isopropenylphenol and phenol, which are then distilled and recovered.

The materials discharged from the system including the cleavage reaction vessel and the distillation column in the invention are usually the cleavage product taken from the top of the distillation column and the residue of the cleavage reaction vessel. However, in the method, the impurities such as chroman derivatives and flavan derivatives are concentrated in the residue of the cleavage reaction vessel. The residue is also a useful phenol-based compound and applied to various utilizations. However, according to the utilization, the impurities such as chroman derivatives and flavan derivatives are disliked, and the decrease of these impurities may be desired.

These impurities may be separated and removed from the cleavage residue discharged, but it is not efficient. In the invention, it has been found that by discharging out the impurities such as chroman derivatives and flavan derivatives from the system by side cutting, such a problem can be solved. By the side cutting, the purity of the cleavage product distilled for purification is also increased. This is because, by the side cutting, these impurities are reduced, and the uncleaved bisphenols entrained in the cleavage product are reduced.

It is preferred that the side cutting is carried out in the liquid-phase portion wherein the impurities such as chroman derivatives, flavan derivatives, and the above-described uncleaved bisphenois are concentrated. As the stage of the carrying out side cutting, the state that these impurities are concentrated is good, and the lowermost portion of the distillation column is preferred. The side cutting may be carried out continuously or intermittently, and the side cutting amount is preferably at least 1% by weight of the reflux liquid of the distillation column. There is no particular restriction on the upper limit, but taking into consideration the economy, the upper limit is preferably about 20% by weight or lower.

It is preferred that the cleavage pro duct obtained is circulated and recovered in the production process of bisphenols such as bisphenol A. The cleavage product recovered is generally re-combined to bisphenol A in the presence of an acidic catalyst, and after crystallization for purification, the product is recovered as bisphenol A.

Then, the invention is explained in more detail with reference to the following Examples. The composition analysis values described in the Examples are those measured by the following method.

(1) Composition Analysis

The composition was measured using a liquid chromatograph (manufactured by JASCO Corporation, Type: PU-980, Detector: UV-970, Column: ODS-filler size 5 $\mu$m) and using an acetonitrile/water-based gradient as a developing solvent.

EXAMPLE 1

A mixture containing 60% by weight of bisphenol A, 11% by weight of 4-(4-hydroxyphenyl)-2,2,4-trimethylchroman (herein-after, is referred to as co-dimer), 5% by weight of 2-(4-hydroxyphenyl)-2,4,4-trimethylchroman (hereinafter, is referred to as flavan), and 24% by weight of high-boiling substances was subjected to a cleavage reaction using a cleavage reactor having a packing column in a distillation portion (upper portion) disposed therein. In the packing portion of the packing column was packed a regular packing having a height of 60 cm (Melapack, a trade name, manufactured by SUMITOMO HEAVY INDUSTRIES, LTD.), and in a lower portion thereof was disposed a liquid collector serving as a demister. In the cleavage reaction vessel was continuously supplied a mixture of bisphenols, and a cleavage reaction was carried out in the presence of a sodium hydroxide catalyst at a temperature of 230° C. under a reduced pressure of 60 mmHg. The temperature of the packing portion of the packing column was 160° C., and the pressure was controlled to a reduced pressure of 58 mmHg. The distillate of the cleavage reaction vessel was continuously taken out therefrom in a vapor state, supplied to the packing column, and after being condensed by a condenser, the condensate was refluxed from the upper portion of the packing column at a reflux ratio of 0.3. When the continuous operation was carried out for 2 months, the pressure increase of the packing portion was not observed. As the result of carrying out the composition analysis of the distillate of the packing column, phenol was 36% by weight, 4-isopropenylphenol 63% by weight, the co-dimer 0.3% by weight, flavan 0.2% by weight, and non-identified substances 0.5% by weight, and 85% by weight of the supplied raw materials were recovered.

Also, in this case, the cleavage residue contained 24% by weight the co-dimer and 12% by weight flavan.

EXAMPLE 2

By following the same procedures as in Example 1 except that from the liquid collecting portion in a lower portion of the packing column, a liquid amount corresponding 5% by weight of the reflux liquid of the distillation column was continuously discharged out, the cleavage reaction was carried out. As the results of analyzing the composition of the cleavage distillate, phenol was 36.2% by weight, 4-isopropenylphenol 63.2% by weight, the co-dimer 0.2% by weight, flavan 0.1% by weight, and non-identified substances 0.3% by weight. The cleavage residue contained 5% by weight the co-dimer and 2% by weight flavan.

Comparative Example 1

By following the same procedures as in Example 1 except that the packing column of the distilling portion of the cleavage reaction vessel was removed and that the distillate was directly discharged out from the system, the cleavage reaction was carried out. As the result of analyzing the composition of the cleavage distillate, phenol was 31% by weight, 4-isopropenylphenol 54% by weight, the co-dimer 9% by weight, flavan 5% by weight, and non-identified substances 1% by weight.

Comparative Example 2

By following the same procedures as in Example 1 except that the reflux ratio of the distillation step was changed to 5, the cleavage reaction was carried out. As the result of analyzing the composition of the cleavage distillate, phenol was 35% by weight, 4-isopropenylphenol 62% by weight, the co-dimer 0.3% by weight, flavan 0.2% by weight, and non-identified substances 2.5% by weight. The amount of the distilled liquid was 70% by weight of the supplied amount to the cleavage reaction vessel.

Comparative Example 3

By following the same procedures as in Example 1 except that the temperature of the packing portion of the packing column was changed to 110° C., the cleavage reaction was carried out. At the time after passing one month since the initiation of the continuous operation, the pressure of the packing portion began to raise, and after passing two months, the operation became difficult, whereby the operation was stopped.

As described above, according to the invention, because the cleavage reaction product is supplied in a vapor state to a distillation column, the occurrence of the polymerization of highly reactive isopropenylphenol, etc. is prevented, and the formations of oligomers such as dimers and trimers can be restrained. Accordingly, phenol and isopropenylphenol having high purity can be obtained. Also, when the distillate of the reflux step (reflux residue) is circulated to the production step of, for example, bisphenol A, etc., the quality of bisphenol A as the product is not lowered, the purity thereof is rather improved, and the production cost is reduced. Furthermore, by side cutting the impurities such as chroman derivatives and flavan derivatives in the distillation column, these impurities can be prevented from being concentrated in the residue of the cleavage reaction vessel, and the effect of reducing chromans and flavans in the cleavage residue can be obtained.

What is claimed is:

1. A cleavage method of bisphenols for producing a product containing isopropenylphenol and phenol by cleaving a mixture containing bisphenols together with chroman derivatives and flavan derivatives formed as by-products in the production process of bisphenols, which comprises
    (1) a cleavage step of supplying the mixture containing bisphenols together with chroman derivatives and flavan derivatives formed as by-products in the production process of bisphenols to a cleaving vessel and carrying out a cleavage reaction in the presence of a basic or acidic catalyst at a temperature of from 150 to 260° C. under a reduced pressure condition of not higher than 300 mmHg,
    (2) a distillation step of supplying the cleavage step product formed in the cleavage step in a vapor state to a distillation column and distilling at a temperature of from 130 to 200° C. under a reduced pressure condition of not higher than 300 mmHg, and
    (3) a reflux step of condensing the distillate from the distillation step, refluxing a part thereof to the distillation step at a reflux ratio of from 0.01 to 3, and discharging out the residue from the system.

2. The cleavage method of bisphenols according to claim 1, wherein the bottom liquid of the distillation step is returned to the cleavage step.

3. The cleavage method of bisphenols according to claim 1, wherein at least 1% by weight of the reflux liquid of the distillation column is taken out from the system by side cutting.

4. The cleavage of bisphenols according to claim 3, wherein the portion taken out by the side cutting is the lowermost portion of the distillation column.

5. The cleavage method of bisphenols according to claim 1, wherein the distillation column is a packing column.

6. The cleavage method of bisphenols according to claim 5, wherein a demister is disposed in a lower portion of the distillation column.

7. The cleavage method of bisphenols according to claim 6, wherein the demister disposed in a lower portion of the distillation column is a liquid collector in a lower portion of the column.

8. The cleavage method of bisphenols according to claim 1, wherein the distillation column is formed in an upper portion of the cleavage reaction vessel.

9. The cleavage method of bisphenols according to claim 8, wherein the distillate of the reflux step is introduced into the production process of bisphenols and recovered.

10. The cleavage method of bisphenols according to claim 9, wherein the bisphenol is bisphenol A.

11. The cleavage method of bisphenols according to claim 8, wherein the distillate of the reflux step is introduced into the production process of bisphenols and recovered.

12. The cleavage method of bisphenols according to claim 7, wherein the distillate of the reflux step is introduced into the production process of bisphenols and recovered.

13. The cleavage method of bisphenols according to claim 6, wherein the distillate of the reflux step is introduced into the production process of bisphenols and recovered.

14. The cleavage method of bisphenols according to claim 5, wherein the distillate of the reflux step is introduced into the production process of bisphenols and recovered.

15. The cleavage method of bisphenols according to claim 4, wherein the distillate of the reflux step is introduced into the production process of bisphenols and recovered.

16. The cleavage method of bisphenols according to claim 3, wherein the distillate of the reflux step is introduced into the production process of bisphenols and recovered.

17. The cleavage method of bisphenols according to claim 2, wherein the distillate of the reflux step is introduced into the production process of bisphenols and recovered.

18. The cleavage method of bisphenols according to claim 1, wherein the distillate of the reflux step is introduced into the production process of bisphenols and recovered.

19. The cleavage method of bisphenols according to claim 8, wherein the bisphenol is bisphenol A.

20. The cleavage method of bisphenols according to claim 7, wherein the bisphenol is bisphenol A.

21. The cleavage method of bisphenols according to claim 6, wherein the bisphenol is bisphenol A.

22. The cleavage method of bisphenols according to claim 5, wherein the bisphenol is bisphenol A.

23. The cleavage method of bisphenols according to claim 4, wherein the bisphenol is bisphenol A.

24. The cleavage method of bisphenols according to claim 3, wherein the bisphenol is bisphenol A.

25. The cleavage method of bisphenols according to claim 2, wherein the bisphenol is bisphenol A.

26. The cleavage method of bisphenols according to claim 1, wherein the bisphenol is bisphenol A.

* * * * *